United States Patent
Briegel et al.

(10) Patent No.: US 7,128,813 B2
(45) Date of Patent: Oct. 31, 2006

(54) PROCESS FOR MANUFACTURING HIGH PURITY METHACRYLIC ACID

(75) Inventors: Keith Frederick Briegel, Houston, TX (US); James Clarence Day, North Wales, PA (US); Michael Stanley DeCourcy, Houston, TX (US); Donald Alan Ebert, Friendswood, TX (US); Jamie Jerrick John Juliette, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 319 days.

(21) Appl. No.: 10/420,273

(22) Filed: Apr. 22, 2003

(65) Prior Publication Data

US 2003/0205451 A1 Nov. 6, 2003

Related U.S. Application Data

(60) Provisional application No. 60/376,710, filed on May 1, 2002.

(51) Int. Cl.
*B01D 3/14* (2006.01)
*B01D 3/34* (2006.01)
*B01D 3/42* (2006.01)
*C07C 51/44* (2006.01)
*C07C 57/04* (2006.01)

(52) U.S. Cl. .................. 203/1; 203/8; 203/49; 203/38; 203/74; 203/75; 203/77; 203/78; 203/80; 203/99; 203/DIG. 9; 203/DIG. 19; 203/DIG. 21; 562/600

(58) Field of Classification Search .................. 203/1, 203/8, 49, 80, 9, 38, DIG. 21, DIG. 9, DIG. 19, 203/74–75, 77–78, 99; 562/532, 600
See application file for complete search history.

(56) References Cited

U.S. PATENT DOCUMENTS 3,432,401 A * 3/1969 Tcherkawsky ............... 203/15

(Continued)

FOREIGN PATENT DOCUMENTS

EP 0102642 1/1986

(Continued)

OTHER PUBLICATIONS

J.J. Kurland: "Quantitative Aspects of Synergistic Inhibition of Oxygen and p-Methoxyphenol in Acrylic Acid Polymerization" Journal of Polymer Science: Polymer Chemistry Edition. vol. 18 (1980) p. 1139-45.

*Primary Examiner*—Virginia Manoharan
(74) *Attorney, Agent, or Firm*—Alan Holler; Marcella Bodner

(57) ABSTRACT

A process for the high yield production of high purity glacial methacrylic acid ("HPMAA") with minimization of decomposition of hydroxy isobutyric acid (HIBA). The HPMAA is substantially pure, specifically 99% pure or greater with a water content of 0.05% or less. This improved process involves the steps of providing a crude MAA stream which was formed by hydrolyzing acetone cyanohydrin and, therefore, includes HIBA which is an intermediate product of the hydrolysis reaction, and purifying that crude methacrylic acid stream in a series of successive distillation steps.

9 Claims, 3 Drawing Sheets

U.S. PATENT DOCUMENTS

| | | |
|---|---|---|
| 3,689,541 A | 9/1972 | Sennewald et al. |
| 3,798,264 A | 3/1974 | Kubota et al. |
| 3,844,903 A * | 10/1974 | Willersinn et al. ............ 203/51 |
| 3,859,175 A * | 1/1975 | Ohrui et al. .................. 203/46 |
| 3,988,213 A | 10/1976 | Yoshida et al. |
| 4,021,310 A * | 5/1977 | Shimizu et al. ................ 203/8 |
| 4,142,058 A * | 2/1979 | Matsumura et al. ........ 562/600 |
| 4,199,410 A | 4/1980 | Ohrui et al. |
| 4,260,821 A | 4/1981 | Benjamin et al. |
| 4,554,054 A * | 11/1985 | Coyle .......................... 203/15 |
| 5,393,918 A | 2/1995 | Dobson et al. |
| 2002/0192132 A1 | 12/2002 | Carlson, Jr. et al. |
| 2004/0267050 A1 * | 12/2004 | DeCourcy et al. .......... 562/600 |

FOREIGN PATENT DOCUMENTS

| | | |
|---|---|---|
| EP | 0656343 | 6/1995 |
| EP | 0937488 | 8/1999 |
| EP | 0999200 | 5/2000 |
| EP | 1044957 | 10/2000 |
| EP | 1059281 | * 12/2000 |

* cited by examiner

PROCESS FOR MANUFACTURING HIGH PURITY METHACRYLIC ACID

CROSS REFERENCE TO RELATED PATENT APPLICATION

This is a non-provisional application of prior pending U.S. provisional application Ser. No. 60/376,710 filed on May 1, 2002.

The present invention is related to a process for the production of substantially pure methacrylic acid that is at least 99% pure further having 0.05% or less water content.

Methacrylic acid ("MAA") and methacrylate esters such as methyl methacrylate ("MMA") are used in a wide variety of applications. Typical end-use applications include: acrylic plastic sheeting; molding resins; polyvinyl chloride modifiers; processing aids; acrylic lacquers; floor polishes; sealants; auto transmission fluids; crankcase oil modifiers; automotive coatings; ion exchange resins; cement modifiers; water treatment polymers; electronic adhesives; metal coatings; and acrylic fibers. MAA and methacrylate esters are especially prized in these applications and others because of the hardness they impart to the products in which they are used. They also enhance chemical stability and light stability, as well as ultraviolet radiation resistance, of the products in which they are used. Therefore, MAA and methacrylate esters are often used in applications requiring resins of excellent transparency, strength, and outdoor durability. The MAA market is extremely cost-sensitive; thus, any improvement in process yield, however slight, can result in significant market advantage.

MAA that has a very low percentage by weight of impurities is very desirable. MAA having an impurity level of less than 5% by weight is referred to herein as glacial methacrylic acid ("GMAA"). MAA having an impurity level of less than 1% by weight wherein no more than 0.05% by weight is water is referred to herein as high purity glacial methacrylic acid ("HPMAA").

A conventional process for purifying MAA involves treating the stream with an excess of sulfuric acid to remove some of the water. While this process yields MAA of sufficient purity for use in batch production of direct-esterification esters, it also creates undesirable sulfur-bearing residue. Moreover, the MAA is not purified to 95%, and, therefore, does not meet the requirements of a GMAA or an HPMAA product. Further, such conventional processes for the removal of water from MAA have resulted in increased yield losses and additional waste. Thus, specifications for GMAA (i.e., MAA that is at least 95% pure) and HPMAA (i.e., MAA that is 99% pure further having less than 0.05% water content) have not been met with conventional purification processes.

Therefore, there is an unaddressed need for a method to produce HPMAA at a reduced cost for the manufacturer. Further, there is an unaddressed need to produce HPMAA that consistently meets the product specifications of at least 99% purity and less than 0.5% water.

The present invention solves the problems inherent in the prior art by providing an economical method for producing HPMAA. The present invention involves the purification of MAA to HPMAA via the use of distillation columns to remove various impurities (generally, light impurities, heavy impurities, and water) from an MAA stream such that the resultant product is at least 99% pure MAA with not more than 0.05% water.

Thus, provided herein is a process for the preparation of high purity glacial methacrylic acid, said process comprising:
(i) providing a first distillation column, a second distillation column and a third distillation column;
(ii) feeding a crude methacrylic acid to an upper section of said first distillation column, said crude methacrylic acid comprising methacrylic acid, light ends and heavy ends;
(iii) distilling said crude methacrylic acid in said first distillation column to form a first overhead vapor stream comprising light ends and a first bottom liquid stream comprising methacrylic acid and heavy ends;
(iv) feeding said first bottom liquid stream to a center section of said second distillation column;
(v) distilling said first bottom liquid stream in said second distillation column to form a second overhead vapor stream comprising methacrylic acid and light ends and a second bottom liquid stream comprising heavy ends;
(vi) feeding at least a portion of said second overhead vapor stream to an upper section of said third distillation column;
(vii) distilling said at least a portion of said second overhead vapor stream in said third distillation column to form a third overhead vapor stream comprising light ends and a third bottom liquid stream comprising methacrylic acid wherein said methacrylic acid has an impurity level of not more than 1% by weight wherein no more than 0.05% by weight is water.

Additionally, provided herein is a further process for the preparation of high purity glacial methacrylic acid, said process comprising:
(i) providing a first distillation column, a second distillation column and a third distillation column;
(ii) feeding a crude methacrylic acid to an upper section of said first distillation column, said crude methacrylic acid comprising methacrylic acid, light ends and heavy ends;
(iii) distilling said crude methacrylic acid in said first distillation column to form a first overhead vapor stream comprising light ends and a first bottom liquid stream comprising methacrylic acid and heavy ends;
(iv) feeding said first bottom liquid stream to a center section of said second distillation column;
(v) distilling said first bottom liquid stream in said second distillation column to form a second overhead vapor stream comprising methacrylic acid and light ends and a second bottom liquid stream comprising heavy ends;
(vi) feeding at least a portion of said second overhead vapor stream to an upper section of said third distillation column;
(vii) distilling said at least a portion of said second overhead vapor stream in said third distillation column to form a third overhead vapor stream comprising light ends and a third bottom liquid stream comprising heavy ends, while withdrawing a first liquid sidestream from a lower section of said third distillation column, said first liquid sidestream comprising methacrylic acid wherein said methacrylic acid has an impurity level of not more than 1% by weight wherein no more than 0.05% by weight is water;
(viii) feeding said third bottom liquid stream to said center section of said second distillation column.

Additionally, provided herein is a still further process for the preparation of high purity glacial methacrylic acid, said process comprising:

(i) providing a first distillation column, a second distillation column and a third distillation column;
(ii) feeding a crude methacrylic acid to a center section of said first distillation column, said crude methacrylic acid comprising methacrylic acid, light ends and heavy ends;
(iii) distilling said crude methacrylic acid in said first distillation column to form a first overhead vapor stream comprising methacrylic acid and light ends and a first bottom liquid stream comprising heavy ends;
(iv) feeding at least a portion of said first overhead vapor stream to an upper section of said second distillation column;
(v) distilling said at least a portion of said first overhead vapor stream in said second distillation column to form a second overhead vapor stream comprising light ends and a second bottom liquid stream comprising methacrylic acid and heavy ends;
(vi) feeding said second bottom liquid stream to a center section of said third distillation column;
(vii) distilling said second bottom liquid stream in said third distillation column to form a third overhead vapor stream comprising methacrylic acid wherein said methacrylic acid has an impurity level of not more than 1% by weight wherein no more than 0.05% by weight is water and a third bottom liquid stream comprising heavy ends;
(viii) feeding at least a portion of said third overhead vapor stream to an upper section of said third distillation column;
(ix) feeding said third bottom liquid stream to said center section of said first distillation column.

Moreover, the present invention also provides an apparatus for the preparation of high purity glacial methacrylic acid, said apparatus comprising:
(i) a first distillation column, said first distillation column having a top, a bottom, an upper section adjacent said top, a lower section adjacent said bottom and a center section intermediate said upper section and said lower section;
(ii) a second distillation column, said second distillation column having a top, a bottom, an upper section adjacent said top, a lower section adjacent said bottom and a center section intermediate said upper section and said lower section;
(iii) a third distillation column, said third distillation column having a top, a bottom, an upper section adjacent said top, a lower section adjacent said bottom and a center section intermediate said upper section and said lower section;
(iv) a first inlet line connected to said upper section of said first distillation column;
(v) a first outlet line connected to said top of said first distillation column;
(vi) a second outlet line connecting said bottom of said first distillation column and said center section of said second distillation column;
(vii) a third outlet line connecting said top of said second distillation column with said upper section of said second distillation column and said upper section of said third distillation column;
(viii) a fourth outlet line connected to said bottom of said second distillation column;
(ix) a fifth outlet line connected to said top of said third distillation column;
(x) a sixth outlet line connected to said bottom of said third distillation column.

Additionally, the present invention further provides an apparatus for the preparation of high purity glacial methacrylic acid, said apparatus comprising:
(i) a first distillation column, said first distillation column having a top, a bottom, an upper section adjacent said top, a lower section adjacent said bottom and a center section intermediate said upper section and said lower section;
(ii) a second distillation column, said second distillation column having a top, a bottom, an upper section adjacent said top, a lower section adjacent said bottom and a center section intermediate said upper section and said lower section;
(iii) a third distillation column, said third distillation column having a top, a bottom, an upper section adjacent said top, a lower section adjacent said bottom and a center section intermediate said upper section and said lower section;
(iv) a first inlet line connected to said upper section of said first distillation column;
(v) a first outlet line connected to said top of said first distillation column;
(vi) a second outlet line connecting said bottom of said first distillation column and said center section of said second distillation column;
(vii) a third outlet line connecting said top of said second distillation column with said upper section of said second distillation column and said upper section of said third distillation column;
(viii) a fourth outlet line connected to said bottom of said second distillation column;
(ix) a fifth outlet line connected to said top of said third distillation column;
(x) a sixth outlet line connected to said lower section of said third distillation column;
(xi) a seventh outlet line connecting said bottom of said third distillation column to said center section of said second distillation column.

Additionally, the present invention still further provides an apparatus for the preparation of high purity glacial methacrylic acid, said apparatus comprising:
(i) a first distillation column, said first distillation column having a top, a bottom, an upper section adjacent said top, a lower section adjacent said bottom and a center section intermediate said upper section and said lower section;
(ii) a second distillation column, said second distillation column having a top, a bottom, an upper section adjacent said top, a lower section adjacent said bottom and a center section intermediate said upper section and said lower section;
(iii) a third distillation column, said third distillation column having a top, a bottom, an upper section adjacent said top, a lower section adjacent said bottom and a center section intermediate said upper section and said lower section;
(iv) a first inlet line connected to said center section of said first distillation column;
(v) a first outlet line connecting said top of said first distillation column with said upper section of said first distillation column and said upper section of said second distillation column;
(vi) a second outlet line connected to said bottom of said first distillation column;
(vii) a third outlet line connected to said top of said second distillation column;

(viii) a fourth outlet line connecting said bottom of said second distillation column with said center section of said third distillation column;

(ix) a fifth outlet line connecting said top of said third distillation column with said upper section of said third distillation column and with a product withdrawal line;

(x) a sixth outlet line connecting said bottom of said third distillation column with said center section of said first distillation column.

For clarity, the following definitions are used herein: "top" is the vapor space existing at the extreme top of a distillation column; "bottom" is the liquid sump existing at the extreme bottom of a distillation column; "upper section" is the approximate uppermost ⅓ of the distillation column which is below and adjacent to the "top"; "lower section" is the approximate lowermost ⅓ of the distillation column which is above and adjacent to the "bottom"; "center section" is the approximate ⅓ of the distillation column intermediate the "upper section" and the "lower section"; "line" is a fluidic connection for transporting vapor and/or liquid into a unit, out of a unit or between two or more units, and may include such common peripherals as valves, condensers, flow meters, etc.

Other and further objects, features and advantages will be apparent from the following description of some embodiments of the invention. These embodiments are given for the purpose of disclosure and may be considered in conjunction with the accompanying drawings.

A more complete understanding of the present embodiments and advantages thereof may be acquired by referring to the following description taken in conjunction with the accompanying drawings, in which like reference numbers indicate like features, and wherein.

The present invention involves methods of purifying methacrylic acid ("MAA") to a high-purity methacrylic acid ("HPMAA"). HPMAA is defined as having less than 1% impurities and no more than 0.05% water. The MAA feedstock that could be beneficially purified in the methods of the present invention may be derived from any available industrial process; examples of such process include but are not limited to, an isobutane/isobutylene-based process, an ethylene-based process, or a proplyene-based process. One example of a proplyene-based process for the production of MAA involves an acetone cyanohydrin ("ACH") feedstock being subjected to the steps of hydrolysis, cracking, reaction, and separation. In such a MAA production process, ACH is reacted with an excess of sulfuric acid to hydrolyze the ACH. Then, the hydrolyzed mixture is cracked in a cracking train and then reacted with water to form crude MAA. Finally, the crude MAA stream is then cooled and allowed to separate (essentially a buoyancy separation) into an MAA product stream and a lower layer sulfur-bearing residue stream. The MAA product steam is then purified via the methods of the present invention.

Figure 1:
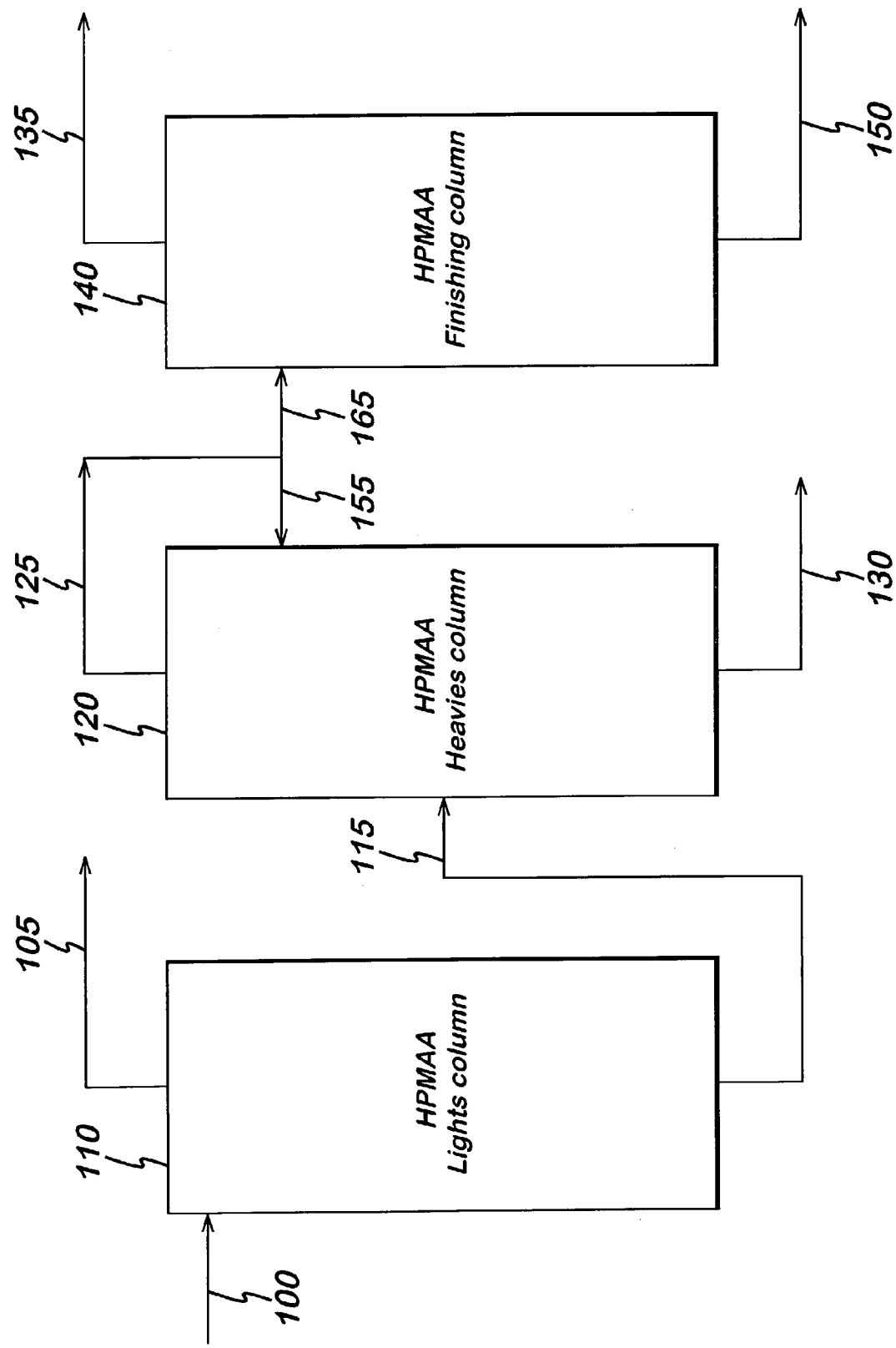
FIG. 1 is a diagram of one embodiment of the present invention of a process for producing HPMAA.

In one embodiment of the method of the present invention to produce HPMAA, shown in FIG. 1, a crude MAA stream is provided via line 100 to the first of three impurity removal apparatus, HPMAA lights column 110. In HPMAA lights column 110, light ends such as acetone and water are removed via line 105. HPMAA lights column 110 also includes column ancillaries, wherein the term "column ancillaries" means any and all secondary equipment and associated piping that is connected to a column, such as vacuum equipment, reboilers, condensers, pumps, and process lines including but not limited to feed lines, bottoms lines, overhead lines, vent lines, inhibitor addition lines, oxygen addition lines, reflux lines, and rundown lines.

HPMAA lights column 110 and its column ancillaries are preferably constructed of materials resistant to corrosion. Suitable materials of construction resistant to corrosive effects include but are not limited to: 300 series stainless steel, 904L, 6-moly stainless steel, HASTELLOY® (e.g., B, B-2, B-3, C-22, and C-276), tantalum, and zirconium. In some embodiments, the manufacturer may reduce construction costs by utilizing covered base metals. "Covered base metal" materials are materials that are generally thought not to be corrosion resistant, such as carbon steel, combined with a covering capable of resisting corrosion such as glass, epoxy, elastomer, fluoropolymer (e.g., TEFLON®), or one of the above-listed corrosion resistant metals. Covered base metals are constructed by placing a covering capable of resisting corrosion over, and optionally bonding the covering to, the base metal. The covering prevents contact between the base-metal and the process stream. Covered base-metal construction is especially preferred for large-diameter piping (3.8 cm or larger nominal diameter) and for heat exchanger tubes in high fluid-velocity service (fluid velocity of 0.15 meter/second or more) and other components, where significant metal thickness (3 mm or more metal thickness) may be used to provide structural strength. The materials described above such as 300 series stainless steel, 904L, 6-moly stainless steel, HASTELLOY® (e.g., B, B-2, B-3, C-22, and C-276), tantalum, zirconium, and covered base-metal materials are hereinafter referred to as "corrosion resistant material."

Internal components such as trays or packing may be used in HPMAA lights column 110, if desired. Internals, if present, may be made from the same materials as the column itself or may be constructed from one or more different materials; for example, the upper portion of the column may contain 300 series stainless steel packing, while the lower portion of the column contains HASTELLOY® B-2 packing. Trays are preferred for use in HPMAA lights column 110. Perforated plate trays are especially preferred, as they have been found to be particularly resistant to MAA polymer accumulation. By the term "perforated plate trays" as used herein is meant any tray comprising a planar portion with a plurality of holes through said planar portion. Optional tray features, including but not limited to weirs, downcomers, baffles, distributors, valves, bubblecaps, and drain holes, may also be present. Examples of perforated plate trays include sieve trays, dualflow trays, and combination valve+ perforation trays. If trays are used, it is preferable that two to ten perforated plate trays be used.

It is also preferred that HPMAA lights column 110 be operated under a vacuum to minimize the temperature at the bottom of the column. For example, in a preferred embodiment, the pressure at the bottom of the column is maintained from 50 mmHg to 80 mmHg, allowing the bottom of the column to be operated from 70° C. to 110° C.

At least one heat exchanger may be used as the heating apparatus for HPMAA lights column 110. Desuperheated steam is the preferred heat source for these exchangers. If a reboiler is used as the heat exchanger, it may be internal or external to the distillation column. Vortex breakers are also useful in the bottom of HPMAA lights column 110.

It is oftentimes useful to add water-soluble or alcohol-soluble polymerization inhibitor to HPMAA lights column 110. Suitable examples include but are not limited to:

Hydroquinone (HQ);
4-methoxyphenol (MEHQ);
4-ethoxyphenol;
4-propoxyphenol;
4-butoxyphenol;
4-heptoxyphenol;
hydroquinone monobenzylether;
1,2-dihydroxybenzene;
2-methoxyphenol;
2,5-dichlorohydroquinone;
2,5-di-tert-butylhydroquinone;
2-acetylhydroquinone;
hydroquinone monobenzoate;
1,4-dimercaptobenzene;
1,2-dimercaptobenzene;
2,3,5-trimethylhydroquinone;
4-aminophenol;
2-aminophenol;
2-N,N-dimethylaminophenol;
2-mercaptophenol;
2-mercaptophenol;
catechol monobutylether;
4-ethylaminophenol;
2,3-dihydroxyacetophenone;
pyrogallol-1,2-dimethylether;
2-methylthiophenol;
t-butyl catechol;
di-tert-butylnitroxide;
di-tert-amylnitroxide;
2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-amino-2,2,6,6-tetramethyl-piperidinyloxy;
4-ethanoloxy-2,2,6,6-tetramethyl-piperidinyloxy;
2,2,5,5-tetramethyl-pyrrolidinyloxy;
3-amino-2,2,5,5-tetramethyl-pyrrolidinyloxy;
2,2,5,5-tetramethyl-1-oxa-3-azacyclopentyl-3-oxy;
2,2,5,5-tetramethyl-3-pyrrolinyl-1-oxy-3-carboxylic acid;
2,2,3,3,5,5,6,6-octamethyl-1,4-diazacyclohexyl-1,4-dioxy;

salts of 4-nitrosophenolate;
2-nitrosophenol;
4-nitrosophenol;
copper dimethyldithiocarbamate;
copper diethyldithiocarbamate;
copper dibutyldithiocarbamate;
copper salicylate;
methylene blue;
iron;
phenothiazine (PTZ);
3-oxophenothiazine;
5-oxophenothiazine;
phenothiazine dimer;
1,4-benzenediamine;
N-(1,4-dimethylpentyl)-N'-phenyl-1,4-benzenediamine;
N-(1,3-dimethylbutyl)-N'-phenyl-1,4-benzenediamine;
N-nitrosophenyl hydroxylamine and salts thereof;
nitric oxide;
nitrosobenzene;
p-benzoquinone;
or isomers thereof; mixtures of two or more thereof; mixtures of one or more of the above with molecular oxygen. The inhibitor(s) may be used alone or combined with a suitable diluent. Preferred diluents include, but are not limited to, MAA, water, and organic mixtures comprising acetone.

Hydroquinone ("HQ") inhibitor is especially preferred for use in HPMAA lights column 110, and it may be added directly, or with a diluent in one or more locations throughout HPMAA lights column 110 and its ancillaries. If used, it is preferred that the inhibitor be added at a rate of 1 kg to 10 kg of HQ per 10,000 kg of HPMAA lights column feed; more preferably 1.3 kg to 8 kg of HQ per 10,000 kg of HPMAA lights column feed; most preferably 1.5 kg to 5 kg of HQ per 10,000 kg of HPMAA lights column feed.

When phenolic inhibitors, such as HQ and MeHQ, are used, it is further preferred that oxygen-containing gas be added to the distillation column to enhance the effectiveness of the inhibitor. The term "oxygen-containing gas," as used herein, refers to any gas comprising from 0.01% up to 100% oxygen. Oxygen-containing gas may be added in one or more locations throughout HPMAA lights column 110 and its column ancillaries. Operating temperatures and pressures impact the flammability limits and oxygen solubility within the purification system, and these properties must be taken into account when determining the appropriate oxygen concentration to be used for the oxygen-containing gas. Considerations of such factors are within the ability of one of ordinary skill in the art, and either pure oxygen or atmospheric air may be commonly employed. Surprisingly, we have found that there is an important factor affecting the efficacy of inhibition within the purification systems not previously considered with respect to oxygen addition—that is the avoidance of high oxygen concentrations within the monomer-containing solution itself. When oxygen concentrations are large relative to inhibitor concentrations, oxygen can actually increase the rate of polymerization by promoting the formation of monomer radicals. For this reason, it is not recommended that oxygen-containing gas be added when no inhibitor is present. Further, it is preferred that when oxygen-containing gas and inhibitors are added to the purification system, that the oxygen-containing gas be added in a prescribed ratio with respect to the inhibitor addition rate. The optimal oxygen to inhibitor ratio will vary with respect to the inhibitor used. When HQ is the selected inhibitor, it is preferred that the ratio of the oxygen-containing gas feed to the HQ inhibitor feed added to the purification system is maintained at 0.65 moles to 10 moles of $O_2$/mole of HQ; more preferably at 1 moles to 8.5 moles of $O_2$/mole of HQ; most preferably at 1.5 moles to 6 moles of $O_2$/mole of HQ. When MEHQ is the selected inhibitor, it is preferred that the ratio of oxygen-containing gas feed to the MEHQ inhibitor feed added to the purification system be maintained at 1 moles to 11.5 moles of $O_2$/mole of MEHQ; more preferably at 1.5 moles to 9 moles of $O_2$/mole of MEHQ; most preferably at 2 moles to 6 moles of $O_2$/mole of MEHQ.

The light ends such as acetone and water, along with some MAA, are taken off of the top of HPMAA lights column 110 via line 105; this stream may be recycled for use elsewhere (e.g., in the MAA process) or may be routed to an acetone recovery vessel. To minimize condensation polymerization, vapor spaces on HPMAA lights column 110 and its ancillaries, including condensers and interconnecting vapor lines, are preferably maintained at a temperature above the dewpoint of MAA; insulation and electric or steam tracing are effective for this purpose.

If stream 105 is condensed after removal from HPMAA lights column 110, coolant having a temperature above 16° C. may be used in the condenser to avoid freezing MAA in the stream. In a preferred embodiment, tempered water in the range of 16° C. to 35° C. is used for the condenser coolant. In one embodiment, a portion of the condensate may be recirculated back to the condenser(s) and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser(s), it may be added through this condensate recirculation stream to improve the distribution of the inhibitor. In an especially preferred embodiment, at least a portion of this condensate recirculation stream may pass through an apparatus that sprays the condensate on the interior surfaces of HPMAA lights column 110 and/or its ancillaries to wash off polymerizable condensates.

In another embodiment, a partial-condenser arrangement is utilized, wherein stream 105 is divided into two or more streams, including at least one MAA/water stream and one water/acetone stream. In this way, the MAA/water stream can be recycled directly into an MAA process and the water/acetone stream can be routed to another process such as an acetone recovery operation, a scrubber, or a flare.

HPMAA lights column 110 bottoms stream 115 contains MAA and heavy ends, such as hydroxy isobutyric acid ("HIBA"), and is substantially free of acetone and water. Stream 115 is fed to the second impurity removal apparatus, HPMAA heavies column 120. In HPMAA heavies column 120, the heavy impurities produced in the crude MAA production process are separated from the MAA. It is particularly important to remove HIBA, as remaining HIBA will tend to decompose in later processing steps. HPMAA heavies column 120 and its column ancillaries are preferably constructed of corrosion resistant material, as described above for HPMAA lights column 110.

Internal components such as trays or packing may be used in HPMAA heavies column 120, if desired. Internals, if present, may be made from the same materials as the column itself or may be constructed from one or more different materials; for example, the upper portion of HPMAA heavies column 120 may contain 300 series stainless steel trays, while the lower portion of the column contains 904L trays. Trays are preferred in HPMAA heavies column 120. Perforated plate trays are especially preferred, as they have been found to be particularly resistant to MAA polymer accumulation. If trays are used, it is preferable that five to fifteen perforated plate trays are used. It is preferred that the heavies column 120 be operated under a vacuum to minimize the bottoms temperature. For example, in a preferred embodiment, the pressure at the bottom of the column be maintained at 60 mmHg to 100 mmHg, allowing the bottom of the column to be operated at 75° C. to 115° C.

At least one heat exchanger may be used as the heating apparatus for HPMAA heavies column 120. Desuperheated steam is preferred as the heat exchanger's heat source. If a reboiler is used as the heat exchanger, it may be internal or external to the column. Vortex breakers are also useful in the bottom of column 120.

It is oftentimes useful to add one or more inhibitors, such as those listed above, to HPMAA heavies column 120 with or without a diluent. MEHQ is a preferred inhibitor and may be added directly, or with a diluent such as MAA, in one or more locations throughout HPMAA heavies column 120 and its ancillaries. If used, MEHQ may be added at a rate of 1 kg to 15 kg of MEHQ per 10,000 kg of HPMAA heavies column feed stream 115; more preferably 1.5 kg to 12 kg of MEHQ per 10,000 kg of HPMAA heavies column feed; most preferably 2 kg to 9 kg of MEHQ per 10,000 kg of HPMAA heavies column feed.

As described above, when phenolic inhibitors, such as HQ and MEHQ, are used, it is further preferred that oxygen-containing gas be added to the distillation column to enhance the effectiveness of the inhibitor. Oxygen-containing gas may be added in one or more locations throughout HPMAA heavies column 120 and its column ancillaries. Operating conditions and concerns and recommended oxygen-to-inhibitor ratios for HPMAA heavies column 120 are identical to those described in connection with HPMAA lights column 110.

Heavy ends, such as HIBA and other impurities, are removed from the bottom of HPMAA heavies column 120 via line 130. The HPMAA heavies column bottoms stream 130 may be disposed of but fuel values are preferably recovered before disposal. Optionally, bottoms stream 130 may be further processed in an independent stripping system to recover residual MAA. In one embodiment of an independent stripping system, bottoms stream 130 may be heated in one or more glass-lined stripping vessels with live steam (steam that comes into direct contact with the MAA-containing heavies column bottoms stream). It is preferred that the stripping vessels be operated at sub-atmospheric pressure to maximize the recovery of MAA. The recovered MAA may be recycled back into a MAA process.

To minimize condensation polymerization, vapor spaces on HPMAA heavies column 120 and its ancillaries, including condensers and interconnecting vapor lines, are preferably maintained at a temperature above the dewpoint of MAA; insulation and electric or steam tracing are effective for this purpose.

The HPMAA heavies column overhead stream 125 contains a significant amount of MAA as well as water, acetone, and other light ends. Overhead stream 125 may be at least partially condensed. If overhead stream 125 is so condensed, tempered water may be used in the condenser(s) to avoid freezing the MAA in the stream. To maintain the required purity of stream 165, it is often necessary to return a portion of the condensate back to HPMAA heavies column 120 via reflux line 155; the fraction of condensate returned may vary from 0% to 100%, depending on the operating conditions of HPMAA heavies column 120 and the MAA purity level desired. In a preferred embodiment, a portion of the condensate may be recirculated back to the condenser(s) and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser(s), it may be added through this condensate recirculation stream to improve the distribution of the inhibitor. In an especially preferred embodiment, at least a portion of this condensate recirculation stream may pass through an apparatus that sprays the condensate on the interior surfaces of HPMAA heavies column 120 and/or its ancillaries to wash off polymerizable condensates. The remaining condensate, comprising MAA and light end impurities, is then transferred via line 165 to HPMAA finishing column 140.

The remaining water, acetone, and other light ends are removed from HPMAA finishing column 140 via overhead stream 135. A partial-condenser arrangement is preferred, wherein overhead stream 135 may be partially condensed into a liquid. If overhead stream 135 is so condensed, tempered water may be used in the condenser(s) to avoid freezing MAA in the stream. To minimize condensation polymerization, vapor spaces on HPMAA finishing column 140 and its ancillaries, including condensers and interconnecting vapor lines, are preferably maintained at a temperature above the dewpoint of MAA; insulation and electric or steam tracing are effective for this purpose. In a preferred embodiment, a portion of the condensate may be recirculated back to the condenser(s) and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser(s), it may be added through this condensate recirculation stream to improve the distribution of the inhibitor. In an especially preferred embodiment, at least a portion of this condensate recirculation stream may pass through an apparatus that sprays the condensate on the interior surfaces of HPMAA finishing column 140 and/or its ancillaries to wash off polymerizable condensates.

HPMAA product stream 150 exits HPMAA finishing column 140 from the bottom portion of the column having purity levels greater than or equal to 99% and containing less than 0.05% water. It is preferred that HPMAA stream 150 be cooled before storage to inhibit polymerization. In some instances, polymer or other undesirable components may be present in the stream; therefore, it may be desirable to filter HPMAA product stream 150 to remove any traces of polymer or other undesirable components prior to storage. HPMAA finishing column 140 and its column ancillaries are preferably constructed of corrosion resistant material, as described above for HPMAA lights column 110. Internal components such as trays or packing may be used in HPMAA finishing column 140, if desired. Internals, if present, may be made from the same materials as HPMAA finishing column 140 itself or may be constructed from one or more different materials. For example, the upper portion of HPMAA finishing column 140 may contain stainless steel packing, while the lower portion of the column may contain zirconium trays. Perforated plate trays are especially preferred, as they have been found to be particularly resistant to MAA polymer accumulation. If trays are used, it is preferable that two to ten perforated plate trays are used.

Preferably, HPMAA finishing column 140 is operated under a vacuum to minimize the temperature in the bottom of the column. For example, in a preferred embodiment, the pressure at the bottom of the column is maintained at 50 mmHg to 80 mmHg, allowing the bottom of the column to be operated between 70° C. to 110° C.

At least one heat exchanger may be used as the heating apparatus for the finishing column. Desuperheated steam is preferred as the heat exchanger's heat source. If a reboiler is used as the heat exchanger, it may be internal or external to the distillation column. Vortex breakers are also useful in the bottom of HPMAA finishing column 140.

It is oftentimes useful to add inhibitors, such as those listed above, to HPMAA finishing column 140 with or without a diluent. Such inhibitor may be added in one or more locations throughout HPMAA finishing column 140 and its ancillaries. The preferred inhibitor for HPMAA finishing column 140 is MEHQ. It is preferred that the inhibitor is added at a rate that does not exceed product inhibitor specifications in the HPMAA product stream 150. Optionally, a variable amount of MEHQ inhibitor may be added directly to the HPMAA product stream 150 to ensure that the HPMAA product stream inhibitor concentration is within final product specifications.

As described above, when phenolic inhibitors, such as HQ and MEHQ, are used, it is further preferred that oxygen-containing gas be added to the distillation column to enhance the effectiveness of the inhibitor. Oxygen-containing gas may be added in one or more locations throughout HPMAA finishing column 140 and its column ancillaries. Operating conditions and concerns and recommended oxygen-to-inhibitor ratios for HPMAA finishing column 140 are identical to those described in connection with HPMAA lights column 110.

Figure 2:
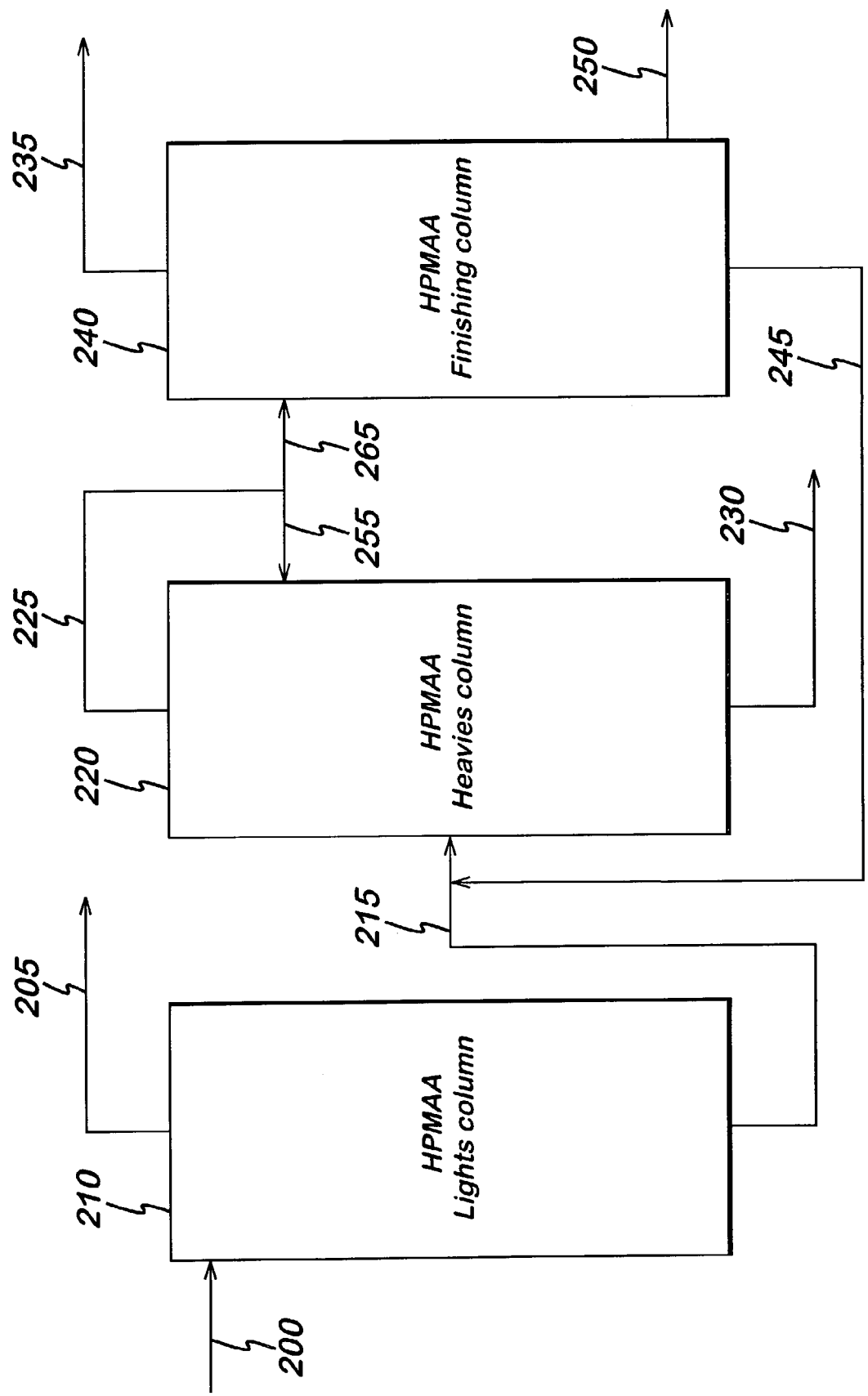
FIG. 2 is a diagram of an alternative embodiment of the present invention of a process for producing HPMAA.

Another embodiment of an HPMAA purification system is shown in FIG. 2 that utilizes a side-draw configuration for the HPMAA product stream. For one skilled in the art, the similarities of this embodiment to the system depicted in FIG. 1 will be evident. The configuration and function of the first two impurity removal apparatus (columns 210 and 220) is essentially the same as described in the previous embodiment (columns 110 and 120, respectively). Similarly, columns 210 and 220 and their column ancillaries are preferably constructed of corrosion resistant material, as previously described for HPMAA lights column 110. The material exiting column 220 via line 265 is a near-HPMAA quality intermediate stream; this stream may be further purified in HPMAA finishing column 240 wherein water and light ends are removed from the upper part of the column through overhead stream 235. In the embodiment of FIG. 2, however, the HPMAA is withdrawn from the side of a third impurity removal apparatus, HPMAA finishing column 240, rather than drawn from the bottom. The finishing column bottoms stream 245, comprising heavy ends, may be recycled, for example to column 220 (as shown) or optionally to column 210, to maximize MAA yield. HPMAA finishing column 240 and its column ancillaries are preferably constructed of corrosion resistant material, as previously described for HPMAA lights column 110.

Water, acetone, and other light ends are removed from HPMAA finishing column 240 via overhead stream 235. A partial-condenser arrangement is preferred, wherein overhead stream 235 is partially condensed into a liquid. If overhead stream 235 is so condensed, tempered water may be used in the condenser(s) to avoid freezing the MAA in the stream. To minimize condensation polymerization, the HPMAA finishing column 240 and its ancillaries, including condensers and interconnecting vapor lines, are preferably maintained at a temperature above the dewpoint of MAA; insulation and electric or steam tracing are effective for this purpose. When trays are used in HPMAA finishing column 240, perforated plate trays are preferred, as they have been found to be particularly resistant to MAA polymer accumulation; two to ten perforated plate trays are especially preferred. In a preferred embodiment, a portion of the condensate may be recirculated back to the condenser(s) and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser(s), it may be added through this condensate recirculation stream to improve the distribution of the inhibitor. In an especially preferred embodiment, at least a portion of this condensate recirculation stream may pass through an apparatus that sprays the condensate on the interior surfaces of HPMAA finishing column 140 and/or its ancillaries to wash off polymerizable condensates.

HPMAA product stream 250 exits HPMAA finishing column 240 from the side of the column having purity levels greater than or equal to 99% and containing less than 0.05% water. Product stream 250 is preferably cooled before storage to inhibit polymerization. Removal of the product stream from the side of the column (known herein as a "side-draw" configuration), instead of from the bottom of the column, allows for improved operation of HPMAA finishing column 240. Because the highest temperature occurs at the bottom of the column, polymer or other undesirable impurities may form and be present in HPMAA product drawn directly from the bottom of the column. While optional filtration of product stream 250 may be used as described in the previous embodiment depicted in FIG. 1, the use of the side-draw configuration in this embodiment may reduce the level of potential impurities in the HPMAA product stream. Thus, the need for filtration may be minimized and the cost of operation reduced, providing an advantage for the manufacturer.

As shown in FIG. 2, heavy end impurities, which may accumulate in the bottom of HPMAA finishing column 240, are removed via stream 245 and recycled back to HPMAA heavies column 220. This recycle step allows the MAA present in stream 245 to be recovered as product in column 220. Any heavy ends and undesirable impurities present in stream 245 will exit column 220 with the other heavy end components in stream 230. It should be noted that, while heavy ends stream 245 may alternatively be recycled back to lights column 210, this step is functionally equivalent to the embodiment shown in FIG. 2 and, as such, will provide similar benefits to the producer.

It is oftentimes useful to add inhibitors, such as those listed above, to HPMAA finishing column 240, optionally with a diluent. Inhibitor may be added in one or more locations throughout HPMAA finishing column 240 and its ancillaries.

The side-draw removal of the HPMAA product stream increases inhibitor options for HPMAA finishing column 240. This is due to the fact that inhibitors are generally heavy components that exit the distillation column through the bottoms. Thus, when the product stream is drawn from the bottom of the column any added inhibitor exits along with it. By way of contrast, when the product is drawn from the side of the column, all of the inhibitor is not drawn off with the product, rather the inhibitor drops to the bottom of the column for removal. Thus, in the embodiment illustrated in FIG. 1 only those inhibitors which are within the final product specification may be used in HPMAA finishing column 140; whereas, in the embodiment illustrated in FIG. 2 a wider variety of inhibitors may be employed in HPMAA finishing column 240.

PTZ is particularly useful for minimizing polymer formation in the bottoms of column 240 and is preferred. If used, PTZ is preferably added (optionally with a diluent) at a rate of 0.005 kg to 8 kg of PTZ per 10,000 kg of HPMAA finishing column 240 feed; more preferably 0.01 kg to 5 kg of PTZ per 10,000 kg of HPMAA finishing column 240 feed; most preferably 0.05 kg to 1 kg of PTZ per 10,000 kg of HPMAA finishing column 240 feed.

If HQ inhibitor is used, it is preferred that the inhibitor be added (optionally with a diluent) at a rate of 1 kg to 10 kg of HQ per 10,000 kg of HPMAA finishing column 240 feed; more preferably 1.3 kg to 8 kg of HQ per 10,000 kg of HPMAA finishing column 240 feed; most preferably 1.5 kg to 5 kg of HQ per 10,000 kg of HPMAA finishing column 240 feed.

MEHQ inhibitor may also be added to HPMAA finishing column 240 in this embodiment and may be added directly, or with a diluent such as MAA, throughout HPMAA finishing column 240 and its ancillaries. Because of the side-draw configuration of HPMAA finishing column 240, it is possible to use higher MEHQ inhibitor addition rates than in HPMAA finishing column 140. In general, satisfactory performance will be achieved in HPMAA finishing column 240 if the MEHQ addition rates for HPMAA finishing column 140, as described above, are utilized. Optionally, a variable amount of MEHQ inhibitor may be added directly to the HPMAA product stream 250 to ensure that the HPMAA product stream inhibitor concentration is within final product specifications.

As described above, when phenolic inhibitors, such as HQ and MEHQ, are used, it is further preferred that oxygen-containing gas be added to the distillation column to enhance the effectiveness of the inhibitor. Oxygen-containing gas may be added in one or more locations throughout HPMAA finishing column 240 and its column ancillaries. Operating conditions and concerns and recommended oxygen-to-inhibitor ratios for HPMAA finishing column 240 are identical to those described in connection with HPMAA lights column 110.

Figure 3:
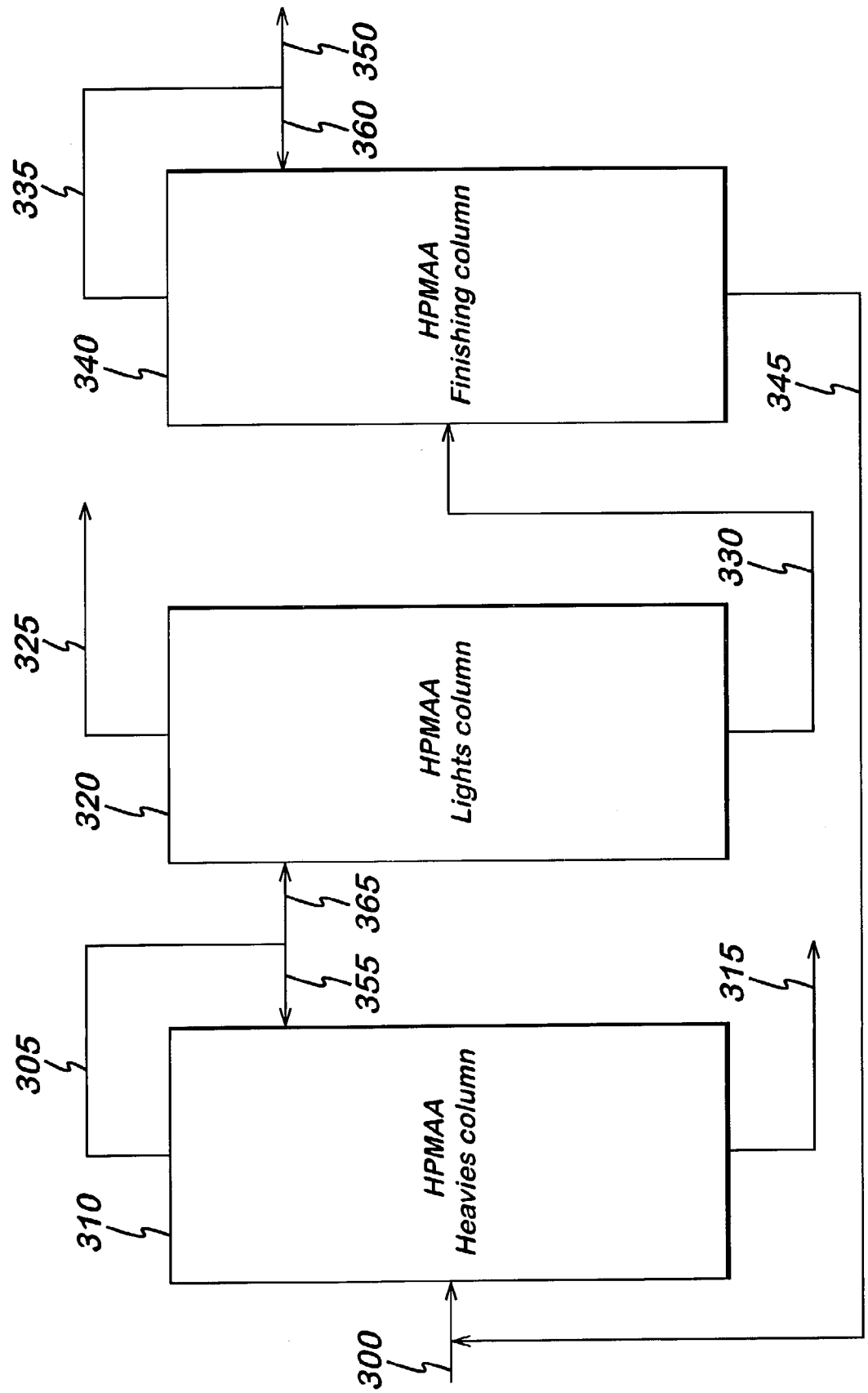
FIG. 3 is a diagram of another embodiment of the present invention of a process for producing HPMAA.

Another embodiment of an HPMAA purification system is shown in FIG. 3. In this embodiment, three impurity removal apparatus are utilized to purify crude MAA stream 300 to HPMAA. Crude MAA stream 300 is initially fed to the first of three impurity removal apparatus, HPMAA heavies column 310. In HPMAA heavies column 310, heavy ends, including HIBA, are removed first from the bottom of the column via line 315. Early removal of heavies in this embodiment prevents HIBA decomposition to water and light ends in the next two columns.

HPMAA heavies column 310 and its column ancillaries are preferably constructed of corrosion resistant material, as previously described for HPMAA light column 110. Internal components such as trays or packing may be used in HPMAA heavies column 310, if desired. Internals, if present, may be made from the same materials as the column itself or may be constructed from one or more different materials. Trays are preferred in HPMAA heavies column 310. Perforated plate trays are especially preferred, as they have been found to be particularly resistant to MAA polymer accumulation. If trays are used, it is preferable that five to fifteen perforated plate trays are used. It is preferred that HPMAA heavies column 310 be operated under a vacuum to minimize the temperature of the bottom of the column. For example, in a preferred embodiment, the pressure at the bottom of the column is maintained at 60 mmHg to 100 mmHg, allowing the bottom of the column to be operated at 75° C. to 115° C. Preferably, at least one heat exchanger may be used as the heating apparatus for HPMAA heavies column 310. Desuperheated steam is preferred as the heat exchanger's heat source. If a reboiler is used as the heat exchanger, it may be internal or external to the column. Vortex breakers are also useful in the bottom of HPMAA heavies column 310.

It is oftentimes useful to add inhibitors such as those listed above, with or without diluents, to HPMAA heavies column 310. HQ inhibitor is especially preferred and may be added directly, or with a diluent such as water, in one or more locations throughout HPMAA heavies column 310 and its ancillaries. If used, it is preferred that the inhibitor be added at a rate of 1 kg to 10 kg of HQ per 10,000 kg of HPMAA heavies column feed; more preferably 1.3 kg to 8 kg of HQ per 10,000 kg of HPMAA heavies column feed; most preferably 1.5 kg to 5 kg of HQ per 10,000 kg of HPMAA heavies column feed.

As described above, when phenolic inhibitors, such as HQ and MEHQ, are used, it is further preferred that oxygen-containing gas be added to the distillation column to enhance the effectiveness of the inhibitor. Oxygen-containing gas may be added in one or more locations throughout HPMAA heavies column 310 and its column ancillaries. Operating conditions and concerns and recommended oxygen-to-inhibitor ratios for HPMAA heavies column 310 are identical to those described in connection with HPMAA lights column 110.

HIBA, other heavy ends, and impurities are removed from the bottom of the heavies column via line 315 and it may be disposed of or recovered for fuel values. Optionally, the heavies column bottoms can be further processed in an independent stripping system to recover residual MAA. In one embodiment of an independent stripping system, the heavies column bottoms are heated in one or more glass-lined stripping vessels with live steam. It is preferred that the stripping vessels be operated at sub-atmospheric pressure to maximize the recovery of MAA.

The HPMAA heavies column overhead stream 305 contains a significant amount of MAA as well as water, acetone, other light ends, and trace amounts of heavy ends. HPMAA heavies column overhead stream 305 is preferably at least partially condensed.

To maintain the required purity of the stream 365, it is often necessary to return a portion of the condensate back to the heavies column via reflux line 355; the fraction of condensate returned may vary from 0% to 100%, depending on the operating conditions of HPMAA heavies column 310 and the MAA purity level desired. The remaining condensate is then transferred via line 365 to a second impurities removal apparatus, HPMAA lights column 320. Tempered water may be used in the heavies column condenser(s) to avoid freezing MAA in the stream. To minimize condensation polymerization, vapor spaces on HPMAA heavies column 310 and its ancillaries, including condensers and interconnecting vapor lines, are preferably maintained at a temperature above the dewpoint of MAA; insulation and electric or steam tracing are effective for this purpose. In a preferred embodiment, a portion of the condensate may be recirculated back to the condenser, and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser, it may be added to this condensate recirculation stream to improve the distribution of the inhibitor. In an especially preferred embodiment, at least a portion of this condensate recirculation stream may pass through an apparatus that sprays the condensate on the interior surfaces of HPMAA heavies column 310 and/or its ancillaries to wash off polymerizable condensates.

HPMAA lights column 320 removes water, acetone, and other light impurities from the MAA via stream 325. HPMAA lights column 320 and its column ancillaries are preferrably constructed of corrosion resistant material, as previously described for HPMAA lights column 110. Internal components such as trays or packing may be used in HPMAA lights column 320, if desired. Internals, if present, may be made from the same materials as the column itself or may be constructed from one or more different materials. Perforated plate trays are especially preferred, as they have been found to be particularly resistant to MAA polymer accumulation. If trays are used, it is preferable that two to ten perforated plate trays are used. It is preferred that HPMAA lights column 320 be operated under a vacuum to minimize the temperature at the bottom of the column. For example, in a preferred embodiment, the pressure at the bottom of the column is maintained at 50 mmHg to 80 mmHg, allowing the bottom of the column to be operated at 70° C. to 110° C. At least one heat exchanger may be used as the heating apparatus for HPMAA lights column 320. Desuperheated steam is preferred as the heat exchanger's heat source. If a reboiler is used as the heat exchanger, it may be internal or external to the column. Vortex breakers are also useful in the bottom of HPMAA lights column 320.

It is oftentimes useful to add one or more inhibitors, such as those listed above, to HPMAA lights column 320. The inhibitors may be added to the column directly, or with a diluent, in one or more locations throughout HPMAA lights column 320 and its ancillaries. PTZ is particularly useful for minimizing polymer formation in the column bottoms and is preferred.

If PTZ is used in HPMAA lights column 320, it is preferably added (optionally with diluent) at a rate of 0.05 kg to 12 kg of PTZ per 10,000 kg of column feed; more preferably 0.1 kg to 10 kg of PTZ per 10,000 kg of column feed; and most preferably 0.4 kg to 5 kg of PTZ per 10,000 kg of column feed.

If HQ is used in HPMAA lights column 320, it is preferably added (optionally with diluent) at a rate of 1 kg to 10 kg of HQ per 10,000 kg of column feed; more preferably 1.3 kg to 8 kg of HQ per 10,000 kg of column feed; most preferably 1.5 kg to 5 kg of HQ per 10,000 kg of column feed.

As described above, when phenolic inhibitors, such as HQ and MEHQ, are used, it is further preferred that oxygen-containing gas be added to the distillation column to enhance the effectiveness of the inhibitor. Oxygen-containing gas may be added in one or more locations throughout HPMAA lights column 320 and its column ancillaries. Operating conditions and concerns and recommended oxygen-to-inhibitor ratios for HPMAA lights column 320 are identical to those described in connection with HPMAA lights column 110.

The MAA, acetone, and water are taken off of the top of HPMAA lights column 320 via line 325. A partial-condenser arrangement is preferred, wherein stream 325 is at least partially condensed into a liquid. If stream 325 is so condensed, tempered water may be used in the condenser(s) to avoid freezing MAA in the stream. To minimize condensation polymerization, vapor spaces on HPMAA lights column 320 and its ancillaries, including condensers and interconnecting vapor lines, are preferably maintained at a temperature above the dewpoint of MAA; insulation and electric or steam tracing are effective for this purpose. In a preferred embodiment, a portion of the condensate may be recirculated back to the condenser and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser, it may be added to this condensate recirculation stream to improve the distribution of the inhibitor. In an especially preferred embodiment, at least a portion of this condensate recirculation stream may pass through an apparatus that sprays the condensate on the interior surfaces of HPMAA heavies column 320 and/or its ancillaries to wash off polymerizable condensates.

A high purity MAA stream 330 with a small amount of heavy ends is removed from the bottom of the lights column and is fed to a third and final impurity removal apparatus, HPMAA finishing column 340. In HPMAA finishing column 340, MAA is separated from the remaining heavy end impurities to produce HPMAA.

HPMAA finishing column 340 and its column ancillaries are preferably constructed of corrosion resistant material, as previously described for HPMAA lights column 110. Internal components such as trays or packing may be used in HPMAA finishing column 340, if desired. Internals, if present, may be made from the same materials as the column itself or may be constructed from one or more different materials. Perforated plate trays are especially preferred, as they have been found to be particularly resistant to MAA polymer accumulation. If trays are used, it is preferable that five to fifteen perforated plate trays are used. HPMAA finishing column 340 is preferably operated such that the decomposition of any remaining trace amounts of HIBA is avoided. Preferably, HPMAA finishing column 340 is operated under a vacuum (i.e., below atmospheric pressure) to minimize bottoms temperature. For example, in a preferred embodiment, the pressure at the bottom of HPMAA finishing column 340 is maintained at 60 mmHg to 100 mmHg, allowing the bottom of HPMAA finishing column 340 to be operated at 75° C. to 115° C.

At least one heat exchanger may be used as the heating apparatus for the finishing column. Desuperheated steam is preferred as the heat exchanger's heat source. If a reboiler is used as the heat exchanger, it may be internal or external to the column. Vortex breakers are also useful in the bottom of HPMAA finishing column 340.

HPMAA having purity levels greater than or equal to 99% and less than 0.05% water leaves HPMAA finishing column 340 via line 335 and is at least partially condensed. Tempered water may be used in the condenser to avoid freezing MAA in the stream. In order to maintain the required purity of the HPMAA product, it is often necessary to return a portion of the condensate back to HPMAA finishing column 340 via reflux line 360; the fraction of condensate returned may vary from 0% to 100%, depending on the operating conditions of HPMAA finishing column 340 and the HPMAA purity level desired. The remaining condensate, exits via HPMAA product stream 350 from the top portion of the column having purity levels greater than or equal to 99% and containing less than 0.05% water. The HPMAA product may be cooled before storage to inhibit polymerization. To minimize condensation polymerization, vapor spaces on HPMAA finishing column 340 and its ancillaries, including condensers and interconnecting vapor lines, are preferably maintained at a temperature above the dewpoint of MAA. Insulation and electric or steam tracing are suitable for this purpose. In a preferred embodiment, a portion of HPMAA finishing column 340 condensate may be recirculated back to the condenser, and optionally to the vapor inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser, it may be added to this condensate recirculation stream to improve the distribution of the inhibitor. In an especially preferred embodiment, at least a portion of this condensate recirculation stream may pass through an apparatus that sprays the condensate on the interior surfaces of HPMAA finishing column 340 and/or its ancillaries to wash off polymerizable condensates.

HIBA and other impurities are removed from the bottom of HPMAA finishing column 340 via line 345. The recovery of the MAA is maximized by recycling this stream to HPMAA heavies column 310.

It is oftentimes useful to add one or more inhibitors, such as those listed above, to HPMAA finishing column 340, optionally with a diluent. Such inhibitor may be added in one or more locations throughout HPMAA finishing column 340 and its ancillaries. PTZ is particularly useful for minimizing polymer formation in the bottom of HPMAA finishing column 340 and is preferred. If used, PTZ is preferably added (optionally with diluent) at a rate of 0.005 kg to 8 kg of PTZ per 10,000 kg of HPMAA finishing column 340 feed; more preferably0.01 kg to 5 kg of PTZ per 10,000 kg of HPMAA finishing column 340 feed; most preferably 0.05 kg to 1 kg of PTZ per 10,000 kg of HPMAA finishing column 340 feed. If HQ is used, it is preferred that the inhibitor be added at a rate from 1 kg to 10 kg of HQ per 10,000 kg of HPMAA finishing column 340 feed; more preferably 1.3 kg to 8 kg of HQ per 10,000 kg of HPMAA finishing column 340 feed; most preferably 1.5 kg to 5 kg of HQ per 10,000 kg of HPMAA finishing column 340 feed.

MEHQ may also be added to HPMAA finishing column 340 directly, or with a diluent such as MAA, in one or more locations in HPMAA finishing column 340 and its associated equipment. If MEHQ is used, it is preferred that the inhibitor be added at a rate from 1 kg to 15 kg of MeHQ per 10,000 kg of feed stream 330. Because the HPMAA product is taken overhead, however, it is not critical to restrict the MEHQ inhibitor addition rate to HPMAA finishing column 340 to this range. To one skilled in the art it will be apparent that, because the HPMAA is taken overhead, it may be possible to make a product within the required specifications even if the preferred inhibitor addition rates are exceeded; however, operation exceeding preferred inhibitor rates will be inefficient.

If more than one inhibitor is introduced directly into HPMAA finishing column 340, the addition rates of the individual inhibitors may be reduced relative to the rates disclosed above. Regardless of the inhibitors used in the finishing column and their respective addition rates, a variable amount of MEHQ inhibitor may be added directly to stream 350 to ensure that the HPMAA product stream inhibitor concentration is within final product specifications.

As described above, when phenolic inhibitors, such as HQ and MEHQ, are used, it is further preferred that oxygen-containing gas be added to the distillation column to enhance the effectiveness of the inhibitor. Oxygen-containing gas may be added in one or more locations throughout HPMAA finishing column 340 and its column ancillaries. Operating conditions and concerns and recommended oxygen-to-inhibitor ratios for HPMAA finishing column 340 are identical to those described in connection with HPMAA lights column 110.

By way of example, and not limitation, the following description, relating to the operation of the HPMAA purification system that is within the scope of this invention, is provided to illustrate the use of the inhibitor in conjunction with an oxygen-containing gas:

EXAMPLE 1

A crude MAA feed stream, comprising greater than 80% MAA, is fed to HPMAA lights column 110 at a rate of 4,545 kg/hr. The pressure at the bottom of the column is 65 mm Hg and the temperature at the bottom of the column is maintained at 90° C. to 100° C. Inhibitor solution comprising 3.5% HQ in water is added in multiple locations throughout the HPMAA lights column and its ancillaries to yield an overall solution feed rate of 23 kg/hr. Atmospheric air is added to the reboiler circulation line at a rate of 5 kg/hr. The resultant ratio of oxygen-containing gas addition to inhibitor is 4.5 moles $O_2$ per mole of HQ, and polymer formation in the distillation column is effectively inhibited.

EXAMPLE 2

An MAA feed stream, comprising greater than 90% MAA, is fed to the HPMAA heavies column 120 at a rate of 9,090 kg/hr. The pressure at the bottom of the column is 60 mm Hg and the temperature at the bottom of the column is maintained at 100° C. to 105° C. Inhibitor solution comprising 2.5% MEHQ in GMAA is added in multiple locations throughout the HPMAA heavies column and its ancillaries to yield an overall solution feed rate of 126 kg/hr. Atmospheric air is added to the reboiler circulation line at a rate of 9 kg/hr. The resultant ratio of oxygen-containing gas addition to inhibitor is 2.6 moles $O_2$ per mole of MEHQ, and polymer formation in the distillation column is effectively inhibited.

The present invention, therefore, is well adapted to carry out the objects and attain both the ends and the advantages mentioned, as well as other benefits inherent therein. While the present invention has been depicted, described, and is defined by reference to particular embodiments of the invention, such references do not imply a limitation on the invention, and no such limitation is to be inferred. The invention is capable of considerable modification, alteration, and substitution of equivalents in form and/or function, as will occur to those of ordinary skill in the pertinent arts. The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A process for the preparation of high purity methacrylic acid with minimization of decomposition of hydroxy isobutyric acid (HIBA), said process comprising:
   (i) using a first distillation column, a second distillation column and a third distillation column;
   (ii) feeding a crude methacrylic acid, which was formed by hydrolyzing acetone cyanohydrin, to an upper section of said first distillation column, said crude methacrylic acid comprising methacrylic acid, light ends and heavy ends, said light ends comprising water and acetone and said heavy ends comprising HIBA;
   (iii) distilling said crude methacrylic acid in said first distillation column, at a pressure between 50 and 80 mmHg and a temperature between 70 and 10° C., to form a first overhead vapor stream comprising light ends and a first bottom liquid stream comprising methacrylic acid and heavy ends;
   (iv) feeding said first bottom liquid stream to a center section of said second distillation column;
   (v) distilling said first bottom liquid stream in said second distillation column, at a pressure between 60 and 100 mmHg and a temperature between 75 and 115° C., to form a second overhead vapor stream comprising methacrylic acid and light ends and a second bottom liquid stream comprising heavy ends;
   (vi) feeding at least a portion of said second overhead vapor stream to an upper section of said third distillation column;
   (vii) distilling said at least a portion of said second overhead vapor stream in said third distillation column, at a pressure between 50 and 80 mmHg and a temperature between 70 and 110° C., to form a third overhead vapor stream comprising light ends and a third bottom liquid stream comprising methacrylic acid wherein said methacrylic acid has an impurity level of not more than 1% by weight wherein no more than 0.05% by weight is water, such that the decomposition of HIBA to water and acetone is minimized.

2. The process for the preparation of high purity methacrylic acid according to claim 1 wherein said second overhead vapor stream is divided into a first portion and a second portion, said first portion being fed to said upper section of said third distillation column, said second portion being fed to an upper section of said second distillation column.

3. A process for the preparation of high purity methacrylic acid with minimization of decomposition of hydroxy isobutyric acid (HIBA), said process comprising:
   (i) using a first distillation column, a second distillation column and a third distillation column;
   (ii) feeding a crude methacrylic acid, which was formed by hydrolyzina acetone cyanohydrin, to an upper section of said first distillation column, said crude methacrylic acid comprising methacrylic acid, light ends and heavy ends, said light ends comprising water and acetone and said heavy ends comprising HIBA;
   (iii) distilling said crude methacrylic acid in said first distillation column, at a pressure between 50 and 80 mmHg and a temperature between 70 and 110° C., to form a first overhead vapor stream comprising light ends and a first bottom liquid stream comprising methacrylic acid and heavy ends;
   (iv) feeding said first bottom liquid stream to a center section of said second distillation column;
   (v) distilling said first bottom liquid stream in said second distillation column, at a pressure between 60 and 100 mmHg and a temperature between 75 and 115° C., to form a second overhead vapor stream comprising methacrylic acid and light ends and a second bottom liquid stream comprising heavy ends;
   (vi) feeding at least a portion of said second overhead vapor stream to an upper section of said third distillation column;
   (vii) distilling said at least a portion of said second overhead vapor stream in said third distillation column, at a pressure between 50 and 80 mmHg and a temperature between 70 and 110° C., to form a third overhead vapor stream comprising light ends and a third bottom liquid stream comprising heavy ends, while withdrawing a first liquid sidestream from a lower section of said third distillation column, said first liquid sidestream comprising methacrylic acid wherein said methacrylic acid has an impurity level of not more than 1% by weight wherein no more than 0.05% by weight is water;
   (viii) feeding said third bottom liquid stream to said center section of said second distillation column.

4. The process for the preparation of high purity methacrylic acid according to claim 3 wherein said second overhead vapor stream is divided into a first portion and a second portion, said first portion being fed to said upper section of said third distillation column, said second portion being fed to an upper section of said second distillation column.

5. A process for the preparation of high purity methacrylic acid with minimization of decomposition of hydroxy isobutyric acid (HIBA), said process comprising:
- (i) using a first distillation column, a second distillation column and a third distillation column;
- (ii) feeding a crude methacrylic acid, which was formed by hydrolyzing acetone cyanohydrin, to a center section of said first distillation column, said crude methacrylic acid comprising methacrylic acid, light ends and heavy ends, said light ends comprising water and acetone and said heavy ends comprising HIBA;
- (iii) distilling said crude methacrylic acid in said first distillation column, at a pressure between 60 and 100 mmHg and a temperature between 75 and 115° C., to form a first overhead vapor stream comprising methacrylic acid and light ends and a first bottom liquid stream comprising heavy ends;
- (iv) feeding at least a portion of said first overhead vapor stream to an upper section of said second distillation column;
- (v) distilling said at least a portion of said first overhead vapor stream in said second distillation column, at a pressure between 50 and 80 mmHg and a temperature between 70 and 110° C., to form a second overhead vapor stream comprising light ends and a second bottom liquid stream comprising methacrylic acid and heavy ends;
- (vi) feeding said second bottom liquid stream to a center section of said third distillation column;
- (vii) distilling said second bottom liquid stream in said third distillation column, at a pressure between 60 and 100 nmHg and a temperature between 75 and 115° C., to form a third overhead vapor stream comprising methacrylic acid wherein said methacrylic acid has an impurity level of not more than 1% by weight wherein no more than 0.05% by weight is water and a third bottom liquid stream comprising heavy ends;
- (viii) feeding at least a portion of said third overhead vapor stream to an upper section of said third distillation column;
- (ix) feeding said third bottom liquid stream to said center section of said first distillation column.

6. The process for the preparation of high purity methacrylic acid according to claim 5 wherein said first overhead vapor stream is divided into a first portion and a second portion, said first portion being fed to an upper section of said first distillation column, said second portion being fed to an upper section of said second distillation column.

7. The process for the preparation of high purity methacrylic acid according to claim 5 wherein said third overhead vapor stream is divided into a first portion and a second portion, said first portion being fed to an upper section of said third distillation column, said second portion being withdrawn as a product stream.

8. A process for the preparation of high purity methacrylic acid, said process comprising:
- (i) using an apparatus for the preparation of high purity methacrylic acid comprising at least one distillation unit, said distillation unit comprising a distillation column and column ancillaries;
- (ii) introducing a crude methacrylic acid feed to said apparatus;
- (iii) purifying said crude methacrylic acid feed by distillation in said at least one distillation unit;
- (iv) introducing 4-methoxyphenol (MEHQ) inhibitor to said at least one distillation unit;
- (v) introducing an $O_2$-containing gas to said at least one distillation unit;
- (vi) adjusting the addition rate of MEHQ to said at least one distillation unit to maintain a ratio of MEHQ addition to crude methacrylic acid feed between 1 kg MEHQ/10,000 kg crude methacrylic acid feed and 15 kg MEHQ/10,000 kg crude methacrylic acid feed;
- (vii) adjusting the addition rate of $O_2$-containing gas to said at least one distillation unit to maintain a molar ratio of $O_2$ to MEHQ between 1.0 mole $O_2$/mole MEHQ and 11.5 moles $O_2$/mole MEHQ.

9. A process for the preparation of high purity methacrylic acid, said process comprising:
- (i) using an apparatus for the preparation of high purity methacrylic acid comprising at least one distillation unit, said distillation unit comprising a distillation column and column ancillaries;
- (ii) introducing a crude methacrylic acid feed to said apparatus;
- (iii) purifying said crude methacrylic acid feed by distillation in said at least one distillation unit;
- (iv) introducing hvdrociuinone (HQ) inhibitor to said at least one distillation unit;
- (v) introducing an $O_2$-containing gas to said at least one distillation unit;
- (vi) adjusting the addition rate of HQ to said at least one distillation unit to maintain a ratio of HQ addition to crude methacrylic acid feed between 1 kg HQ/10,000 kg crude methacrylic acid feed and 10 kg HQ/10,000 kg crude methacrylic acid feed;
- (vii) adjusting the addition rate of $O_2$-containing gas to said at least one distillation unit to maintain a molar ratio of $O_2$ to HQ between 0.65 mole $O_2$/mole HQ and 10 moles $O_2$/mole HQ.

* * * * *